(12) United States Patent
Kumta et al.

(10) Patent No.: US 11,149,166 B2
(45) Date of Patent: Oct. 19, 2021

(54) PEM LAYER-BY-LAYER SYSTEMS FOR COATING SUBSTRATES TO IMPROVE BIOACTIVITY AND BIOMOLECULE DELIVERY

(71) Applicant: UNIVERSITY OF PITTSBURGH—OF THE COMMONWEALTH SYSTEM OF HIGHER EDUCATION, Pittsburgh, PA (US)

(72) Inventors: Prashant N. Kumta, Pittsburgh, PA (US); Sangeetha Kunjukunju, Pittsburgh, PA (US); Nicole J. Ostrowski, Pittsburgh, PA (US); Abhijit Roy, Pittsburgh, PA (US); Boeun Lee, Pittsburgh, PA (US); Madhumati Ramanathan, Hillsboro, OR (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 951 days.

(21) Appl. No.: 14/778,331

(22) PCT Filed: Apr. 3, 2014

(86) PCT No.: PCT/US2014/032790
§ 371 (c)(1),
(2) Date: Sep. 18, 2015

(87) PCT Pub. No.: WO2014/165652
PCT Pub. Date: Oct. 9, 2014

(65) Prior Publication Data
US 2016/0053134 A1    Feb. 25, 2016

Related U.S. Application Data

(60) Provisional application No. 61/807,862, filed on Apr. 3, 2013.

(51) Int. Cl.
C09D 177/04  (2006.01)
A61L 27/58   (2006.01)
(Continued)

(52) U.S. Cl.
CPC .............. *C09D 177/04* (2013.01); *A61F 2/02* (2013.01); *A61L 27/04* (2013.01); *A61L 27/34* (2013.01);
(Continued)

(58) Field of Classification Search
None
See application file for complete search history.

(56) References Cited

U.S. PATENT DOCUMENTS

| | | | |
|---|---|---|---|
| 2004/0083006 A1* | 4/2004 | Ellingsen | A61L 31/148 623/23.57 |
| 2005/0079088 A1* | 4/2005 | Wirth | A61L 27/047 420/402 |

(Continued)

FOREIGN PATENT DOCUMENTS

WO    WO-2005089825 A2 *  9/2005  ............. A61L 27/34

OTHER PUBLICATIONS

Wong, S.Y. et al., Dual functional polyelectrolyte multilayer coatings for implants: permanent microbicidal base with controlled release of therapeutic agents, JACS, 2010, vol. 132, No. 50 pp. 17840-17848.

*Primary Examiner* — Ramsey Zacharia
(74) *Attorney, Agent, or Firm* — Carol A. Marmo; Eckert Seamans Cherin & Mellott

(57) ABSTRACT

The invention relates to polyelectrolyte multilayer coatings and, methods for their preparation and application to sub-
(Continued)

strates to enhance the bioactivity and corrosion protection of the substrates' surface. The invention is particularly suitable for coating substrates employed for medical applications, such as but not limited to medical implant devices for drug and/or biologics delivery in a patient. The substrate has a positive or negative charge. The polyelectrolyte multilayer coatings include at least a first polymer layer and a second polymer layer. The first polymer and second polymer have opposite charges. Each of the polymer layers is individually applied using a layer-by-layer such that an alternating charge multilayer coating is formed.

5 Claims, 5 Drawing Sheets

(51) Int. Cl.
*A61L 27/34* (2006.01)
*A61L 27/04* (2006.01)
*A61L 27/54* (2006.01)
*A61F 2/02* (2006.01)
*B05D 7/00* (2006.01)
*C09D 105/04* (2006.01)
*C09D 167/04* (2006.01)

(52) U.S. Cl.
CPC .............. *A61L 27/54* (2013.01); *A61L 27/58* (2013.01); *B05D 7/58* (2013.01); *C09D 105/04* (2013.01); *C09D 167/04* (2013.01); *A61F 2210/0076* (2013.01); *A61F 2310/00976* (2013.01); *A61L 2300/608* (2013.01); *A61L 2420/08* (2013.01)

(56) References Cited

U.S. PATENT DOCUMENTS

| | | | |
|---|---|---|---|
| 2005/0208100 A1* | 9/2005 | Weber | A61L 27/34 424/426 |
| 2006/0149391 A1* | 7/2006 | Opie | C22C 45/10 623/23.55 |
| 2007/0154513 A1* | 7/2007 | Atanasoska | A61F 2/91 424/423 |
| 2007/0207212 A1 | 9/2007 | Haynie et al. | |
| 2008/0044900 A1* | 2/2008 | Mooney | A61K 38/193 435/375 |
| 2011/0244254 A1 | 10/2011 | Song et al. | |
| 2011/0274744 A1* | 11/2011 | Picart | A61L 27/20 424/445 |
| 2012/0222784 A1* | 9/2012 | Kin | C22C 23/00 148/557 |
| 2013/0006172 A1 | 1/2013 | Desai | |
| 2013/0188255 A1* | 7/2013 | Kameno | B82Y 30/00 359/601 |

\* cited by examiner

PEM LAYER-BY-LAYER SYSTEMS FOR COATING SUBSTRATES TO IMPROVE BIOACTIVITY AND BIOMOLECULE DELIVERY

CROSS REFERENCE TO RELATED APPLICATIONS

This application claims priority under 35 U.S.C. § 119(e) to U.S. Provisional Patent Application Ser. No. 61/807,862, filed Apr. 3, 2013, entitled "Development of SMART Polyelectrolyte Layer-By-Layer Coating Systems on Mg Alloys for Achieving Tailored Corrosion Properties, Improved Bioactivity and Delivery of Inorganic and Organic Biomolecules", which is herein incorporated by reference.

GOVERNMENT SUPPORT AND FUNDING

The invention was made with government support under grant #0812348 awarded by the National Science Foundation. The government has certain rights in the invention.

FIELD OF THE INVENTION

The invention relates to polyelectrolyte multi-layer coatings and, methods for their preparation and application to substrates to enhance the bioactivity and corrosion protection of the substrates' surface. The invention is particularly suitable for coating substrates which are employed for medical applications, such as but not limited to medical implant devices for delivery of biologics in a patient.

BACKGROUND OF THE INVENTION

Biomedical implant devices are known in the art and are commonly used in the practice of orthopedic, craniofacial and cardiovascular implant surgery. These devices may be used for various purposes, such as but not limited to, tissue regeneration and drug or biomolecule delivery. Furthermore, stems are also implanted into a body of a patient to support lumens, for example, coronary arteries. Implant devices include, but are not limited to, scaffolds, such as plates and screws. Biomaterials for the construction of implant devices are typically chosen based on their ability to withstand cyclic load-bearing and compatibility with the physiological environment of a human body. Many of these implant devices are traditionally constructed of polymer or metal. These materials of construction exhibit good biomechanical properties. Metallic biomaterials, in particular, have appropriate properties such as high strength, ductility, fracture toughness, hardness, corrosion resistance, formability, and biocompatibility to make them attractive for most load bearing applications. Polymers, such as polyhydroxy acids, polylactic acid (PLA), polyglycolic acid (PGA), and the like, are known as conventional biomaterials, however, in some instances the strength and ductility exhibited by polymers is not as attractive as that demonstrated by metallic biomaterials. For example, it is known to use stainless steel or titanium biomedical implants for clinical applications which require load-bearing capacities.

Further, metallic and polymer biomaterials are not biodegradable. Thus, there has been an interest and focus to design and develop biodegradable construction materials such that the implant device is capable of degrading over a period of time, e.g., by dissolving in the physiological environment, and therefore, surgery is not required to remove the implant device when it is no longer a medical need. However, in some instances, scaffolds constructed of biodegradable polymer have been found to produce acidic degradation by-products, as well as, low mechanical strength and a lack of osteoconductivity. Magnesium and magnesium alloys are attractive as biomaterials because magnesium is very lightweight, has a density similar to cortical bone, has an elastic modulus close to natural bone, is essential to human metabolism, is a cofactor for many enzymes, and stabilizes the structures of DNA and RNA. Therefore, magnesium-based implants may be degradable in-vivo through simple corrosion and exhibit mechanical properties similar to native bone.

A patient, e.g., human, body innately requires magnesium to function and at low levels the body is capable of absorbing the hydrogen gas released. However, at faster rates the corrosion can result in hydrogen gas pocket formation and implant failure. For clinically relevant magnesium devices, the rates of corrosion should be controlled to ensure functionality and to avoid the accumulation of the hydrogen gas formed during corrosion. It has been found that deposition of a coating composition on the surface of a biomedical implant device can cause a delay in the initial degradation of the magnesium and may improve biocompatibility enabling enhanced osteo-integration between the coated implant and surrounding tissue at the implant site. Known coatings for metal-based implants may be classified as conversion coatings or deposition coatings. Both of these coating classes may be employed to prevent or slow the corrosion of magnesium. Conversion coatings are generally formed in situ through a reaction between the substrate and its environment, and are typically inorganic. For application to magnesium alloys, these coatings are often composed of oxides, phosphates or fluorides. Conversion coatings typically advantageously exhibit good adhesion to the substrate, however, there are disadvantages with respect to the mechanical durability and biocompatibility of these coatings.

Deposition coatings are typically organic or ceramic and are applied through physical interactions with the surface of a metal substrate. For application to magnesium alloy substrates, deposition coatings often require a conversion coating pre-treatment to improve adhesion to the alloy substrates. It has been found that organic deposition coatings which are applied without a conversion coating pre-treatment, e.g., one-step coatings, can demonstrate poor adhesion and corrosion protection of the alloy substrate surface. In comparison, organic deposition coatings applied with a conversion coating pre-treatment, e.g., two-step coatings, have been found to demonstrate improved adhesion and corrosion protection.

A coating process known as "layer-by-layer" deposition may potentially address the disadvantages above-described. This technique results in a polyelectrolyte multilayer (PEM) film formed by static interactions of positively charged and negatively charged polymer chains dissolved in solution. In general, a substrate is incubated in alternating solutions of positively and negatively charged polymers to form thin well-adhered film layers on the substrate. The properties of the film layer assembly may depend on a variety of parameters, such as but not limited to, concentration, pH, molecular weight and additives. These parameters may be selected and controlled to manipulate and customize properties, such as but not limited to, stiffness, hydrophobicity, protein adhesion, degradation rate and drug elusion, surface charge and cell attachment and interaction. Further, the film layer assembly may be manipulated and customized to incorporate drugs, biological molecules and nanoparticles into the coatings.

In the field of biomedical applications, there is a desire to develop biocompatible materials of construction for medical implant devices which are effective for bone regeneration and drug delivery. In accordance with the invention, there is a desire to develop polyelectrolyte layer-by-layer coating systems for deposition on the surface of a pure magnesium or magnesium alloy substrate, degradable or non-degradable, for use as a medical implant device. The layer-by-layer coating may be combined with other coating compositions and methods. Further, it is desired that the coated substrate exhibits improved corrosion properties, bioactivity and delivery of inorganic/organic biomolecules as compared to uncoated substrates.

SUMMARY OF THE INVENTION

In one aspect, the invention provides a coated medical implant device. The implant device includes a charged substrate having a positive charge or a negative charge and a polyelectrolyte multilayer coating. The polyelectrolyte multilayer coating has a first layer which includes a first polymer and a second layer which includes a second polymer. The first layer is deposited on the charged substrate and the second layer is deposited on the first layer. The first polymer has a charge opposite the charge of the charged substrate and the second polymer has a charge opposite the charge of the first polymer.

In certain embodiments, the charged substrate is formed by treating a neutral substrate with a pretreatment agent to convert the neutral substrate to the charged substrate. The pretreatment agent can be selected from alkali metal hydroxide, alkali metal carbonate, phosphating bath including phosphoric acid and/or other metal phosphate salts, hydrogen fluoride, and mixtures thereof.

The polymers can be selected from natural polymers, synthetic polymers and mixtures thereof. In certain embodiments, the polymers may be selected from the group consisting of alginate, poly-L-lysine, poly(lactic-co-glycolic acid), polycaprolactone, poly(allylamine hydrochloride) and mixtures thereof. Further, in certain embodiments, the polymers can include alginate, poly-L-lysine and poly(lactic-co-glycolic acid). In other embodiments, the polymers can include polycaprolactone and poly(allylamine hydrochloride). Each of the polymers is individually deposited to form a layer such that a multilayer coating is formed on the substrate.

Moreover, in certain embodiments, the alternating layers formed by the first and different second polymers can be functionalized, such as by cross-linking, fibronectin immobilization and combinations thereof.

The PEM layer can further include an active substance deposited on or incorporated into at least one of the first and second layers.

In another aspect, the invention provides a method of preparing a coated medical implant device. The method includes charging a neutral substrate to form a positively or negatively charged substrate and forming a polyelectrolyte multilayer coating on the charged substrate. The polyelectrolyte multilayer coating is formed by depositing a first polymer on the charged substrate to form a first layer and depositing a second polymer on the first layer to form a second layer. The first polymer has a charge opposite the charged substrate and the second polymer has a charge opposite the charge of the first polymer.

BRIEF DESCRIPTION OF THE DRAWINGS

A further understanding of the invention can be gained from the following description of the preferred embodiments when read in conjunction with the accompanying drawings in which.

DETAILED DESCRIPTION OF THE PREFERRED EMBODIMENTS

Figure 1:
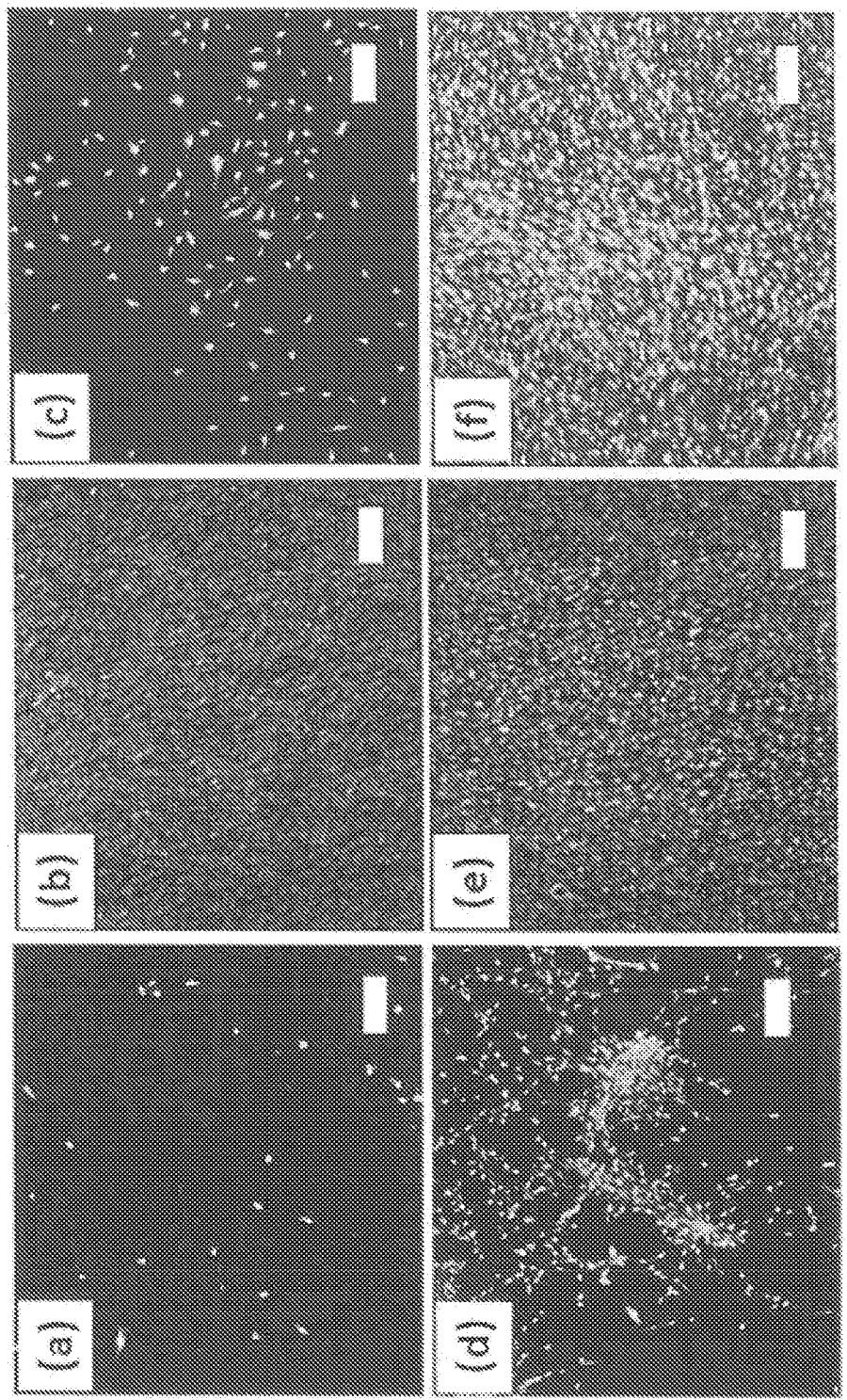
FIG. 1 including views (a) through (f) shows microscopic images of live and dead cells attached on Day 5 to bare AZ31, FAZ31, FAZ31L, FAZ31LC, FAZ31LCP and FAZ31LCF, respectively, in accordance with certain embodiments of the invention.

The invention relates to novel, biocompatible polymer-based coating systems. The systems include a polyelectrolyte multilayer (PEM) coating deposited on a substrate using a conventional layer-by-layer technique. The PEM coating compositions include a plurality of polymers, e.g., at least a first polymer and a second polymer. The layer-by-layer technique may be employed such that a first polymer forms a first layer and a second polymer forms a second layer. Subsequently, alternating deposition of the first and second polymers may be conducted to form a multilayer coating which has alternating layers of the first and second polymers.

The substrate for use in the invention may be selected from a wide variety of substrate materials known in the art for constructing medical implant devices. Suitable substrates include magnesium metal, magnesium alloy, iron metal, iron alloy, ferrous metal and ferrous alloys. The substrates may be degradable or non-degradable. In preferred embodiments, the substrate is degradable. In particular, the substrate may be composed of magnesium alloy or iron alloy.

Non-limiting examples of suitable substrates include those described in PCT Application having International Application No. PCT/US2012/05839 entitled "Biodegradable Metal Alloys" filed on Oct. 5, 2012 and based on U.S. Provisional Patent Application 61/544,127 entitled "Biodegradable Metal Alloys" filed on Oct. 6, 2011; and U.S.

Provisional Patent Application 61/710,338 entitled "Biodegradable Iron-Containing Compositions, Methods of Preparing and Applications Therefor" filed on Oct. 5, 2012, which are incorporated in their entirety herein by reference.

In certain embodiments, the substrates of the invention may be constructed of compositions including magnesium and/or iron. Further, the magnesium and/or iron compositions may contain one or more of zirconium, manganese, calcium, yttrium and zinc. For example, suitable compositions include a combination, e.g., mixture or blend, of magnesium, iron, manganese and calcium, or a combination, e.g., mixture or blend, of magnesium, iron, zirconium and calcium, or a combination, e.g. mixture or blend, of magnesium, iron zinc and calcium. The amount of each of the components in the combinations/compositions can vary and in general, the amounts are selected such that the resulting combinations/compositions are within acceptable non-toxic limits, sufficiently biocompatible and degradable over a period of time. For example, the components and their amounts may be selected such that the combinations and compositions exhibit corrosion resistance in the presence of water and body fluids which allow for suitable in vitro use in a physiological environment, e.g., patient body, and exhibit corrosion resistance with minimal or no evolution of hydrogen gas as the evolution of hydrogen, e.g., hydrogen bubbles, may cause complications in a patient body.

physiological characteristics of the patient, in vitro site of implantation and medical use of the device. Non-limiting examples of suitable other components include aluminum, silver, cerium and/or strontium.

In certain embodiments, the metal elements of the compositions are alloyed by employing high energy mechanical alloying (HEMA) and uniaxial or isostatic compaction and sintering.

In accordance with the invention, the substrate has a positive or negative electrical charge associated therewith. A neutral substrate may be pretreated to form the charged substrate. Various pretreatment agents and techniques are known in the art for this purpose. In certain embodiments, a neutral substrate is at least partially coated with a pretreatment agent, e.g., oxidizing solution, to produce a pretreated, e.g., oxidized/charged, substrate. Suitable pretreatment agents include, but are not limited to, alkali metal hydroxide, such as sodium hydroxide (NaOH), alkali metal carbonates, phosphating bath including phosphoric acid ($H_3PO_4$) and/or other metal phosphate salts, hydrogen fluoride (HF), and mixtures thereof. Without intending to be bound by any particular theory, application of the pretreatment agent is effective to convert the substrate to hydroxide, fluoride, oxide or phosphate.

Table 1 shows various conversion/pretreatment coatings for a magnesium containing substrate.

TABLE 1

Pretreatment/Conversion Coatings

| Conversion Coatings | Concentration Range | Preferred Coating | Thickness |
|---|---|---|---|
| Hydroxide ($Mg(OH)_2$) | Treating soln is NaOH, 0.01M through 25M in water. | 5.0M NaOH in DI water on AZ31 at 60° C. | 10 nm-1000 um* |
| Fluroide (MgF) | Treating soln is HF, 0.01M thru pure HF as HF and water are fully miscible, thru any temp. range. | 48-51 wt % HF in DI water on AZ31 at 22° C. | 10 nm-1000 um |
| Oxide (MgO) | Treating soln NaOH (as above) and/or thermal treatment. | | 10 nm-1000 um |
| Phosphate ($Mg_3(PO_4)_2$) | Treating soln $H_3PO_4$ or other $PO_4$ salt solution (Na K $NH_4$, Ca, etc), 0.01M thru solubility limit per salt and temp. | | 10 nm-1000 um |
| Silicate | Treating soln inorganic and organic salts of silicone e.g., $Na_2SiO_3$, 0.01M thru solubility limit based on salt and temp. | | 10 nm-1000 um |
| Hydroxyapatite | Treating soln comps. of simple salts of calcium and phosphate or other simulated body fluid solutions, 0.01M thru solubility ranges based on salt combinations and temp. | | 10 nm-1000 um |

*"um" means micron.

It is contemplated that other components may be added to the compositions provided that the non-toxicity, biocompatibility and degradability remain within acceptable limits. Acceptable non-toxic limits and time frames for degradation can vary and can depend on the particular physical and The PEM coating includes natural and/or synthetic polymers, such as but not limited to, natural polysaccharide and synthetic poly-amino acid-based polyelectrolytes. Generally, suitable polymers include any positively or negatively charged polymer which may be degradable through aqueous solution mediated or cellular mediated mechanisms (e.g., hydrolytic, thermal, enzymatic or photolytic). Non-limiting examples of suitable polymers include polyesters, polyanhydrides, polyorthoesters, polyphosphazenes, polyphosphoesters, and combinations thereof. The polymers may be selected from alginate (ALG), poly-L-lysine (PLL), poly (lactic-co-glycolic acid) (PLGA), polycaprolactone (PCL), poly(allylamine hydrochloride) (PAH), polyacrylic acid (PAA), heparin (HEP), hyaluronic acid (HA), polystyrene sulfonate (PSS), poly-L-glutamic acid (PGA), chitosan (CHI), polyethyleneimine (PEI), polydiallyldimethylammonium chloride (PDAC) and, mixtures and combinations thereof. In certain embodiments, suitable polymer combinations or pairings include ALG coupled with PLL and PLGA or PCL coupled with PAH. In other embodiments, ALG and PLL are employed.

The invention also relates to methods of preparing the biocompatible multilayer coating systems. The PEM coating is formed by a plurality of polymer layers which are deposited using a conventional layer-by-layer technique. Typically, more than one polymer or polymer composition is employed and each polymer or polymer composition is individually deposited to form a polymer layer. For example, wherein a PEM coating includes two polymers, a first polymer is deposited to form a first layer and a second polymer is deposited on the first layer to form a second layer. Additional layers may be formed by repeating the alternating deposition of the first polymer and second polymer. The initial layer of the PEM coating may be deposited directly on the treated, e.g. charged substrate. The selection of the first and second polymers is such that the first and second polymers have charges that are different, e.g., opposite, from each other and furthermore, the initial polymer deposited on the treated substrate has a charge that is different, e.g., opposite, from the substrate charge. For instance, if the substrate has a positive charge, the initial or first polymer deposited thereon is a polymer having a negative charge. Subsequently, the next or second polymer deposited on the first polymer layer is a polymer having a positive charge. Alternating layers can be formed until a desired coating thickness is achieved. Further, more than two different polymers can be employed for forming the alternating layers.

In certain embodiments, the first polymer and/or the second polymer may include a mixture or blend of polymers. Moreover, the first polymer and/or second polymer may include additional compounds and additives that are known for use in preparing coating compositions. For example, when a third polymer is used it may be combined with one of the first polymer and the second polymer, and deposited to form a mixed or blended polymer layer or the third polymer may be individually deposited to form a third polymer layer.

The layer-by-layer technique generally includes alternately depositing the polymers on the substrate. Accordingly, interfacing layers having different, e.g., opposite, charges. Certain embodiments include forming polymer solutions, such as ALG and PLL solutions, and alternately dipping the substrate into each of the polymer solutions to form a multilayer coating on the substrate which results in alternating layers of ALG and PLL.

The thickness of the PEM coating may vary and typically has a thickness of from about 1 um to about 1000 um.

The concentration of the polymers may vary and in certain embodiments, the polymer is present in an amount of greater than 0 to about 100 mg/mL of the coating solution. In certain preferred embodiments, the polymer is present in an amount from about 0.05 to about 10.0 mg/mL of the coating solution.

In certain embodiments, one or more layers of the PEM coating may be functionalized. Each layer may be functionalized or more typically, the surface of the outer layer (i.e., the final polymer layer of the PEM coating) is functionalized. Surface functionalization can include chemical cross-linking and fibronectin immobilization for use in changing the surface properties of the substrate, such as influencing cellular activity. Cross-linking agents and techniques can employ carbodiimide 1-ethyl-3-(3-dimethylaminopropyl) carbodiimide (EDC), N-hydrosulfosuccinimide, (sulfo-NHS), glutaraldehyde and, mixtures and combinations thereof.

It is generally known in the art of medical implant devices to attach or incorporate active substances. The coated substrates described herein can have at least one active substance attached thereto. In certain embodiments, the active substance may be attached to or deposited on one or more layers of the PEM coating. In these embodiments, the active substance may be provided between the polymer layers of the PEM coating. Further, the active substance may be deposited on the surface of the final outer polymer layer. In certain other embodiments, the active substance may be incorporated within the polymer, e.g., composition, which forms the one or more layers of the PEM coating. As used herein, the term "active substance" describes a molecule, compound, complex, adduct and/or composite that exhibits one or more beneficial activities such as therapeutic activity, diagnostic activity, biocompatibility, corrosion, and the like. Active substances that exhibit a therapeutic activity can include bioactive agents, pharmaceutically active agents, drugs and the like. Non-limiting examples include, but are not limited to, gene transfecting agents, bone growth promoting agents such as growth factors, drugs, proteins, antibiotics, antibodies, ligands, DNA, RNA, peptides, enzymes, vitamins, cells and the like, and combinations thereof. In certain embodiments, the drugs include gentamycin, paclitaxel, and diclofenac, and the biologics include BSA, BMP-2, VEGF, BMPs, TGF, FGF and PDGF.

Without intending to be bound by any particular theory, it is believed that application of the conversion and PEM coatings to the surface of a biomedical implant device will provide improved biocompatibility, improved osteo-integration, controlled corrosion resistance, and controlled delivery of active substance(s) from the implant surface.

The coated medical implant devices include, but are not limited to, scaffolds. Non-limiting examples of scaffolds include, but are not limited to plates, meshes, staples, screws, pins, tacks, rods, suture anchors, tubular mesh, coils, x-ray markers, catheters, endoprostheses, pipes, shields, bolts, clips or plugs, dental implants or devices, graft devices, bone-fracture healing devices, bone replacement devices, joint replacement devices, tissue regeneration devices, cardiovascular stents, nerve guides, surgical implants and wires. In a preferred embodiment, the medical devices include fixation bone plates and screws, temporamandibular joints, cardiovascular stents, and nerve guides.

The following Table 2 shows suitable polymers for use in certain embodiments of the invention to form the PEM coating.

TABLE 2

Suitable Polymers
Non-limiting examples of polymers for PEM coatings for application to charged substrates.

| Anionic Polymer | Cationic Polymers | Concentration Ranges | Preferred Polymers and Concentration |
|---|---|---|---|
| | Poly-L-lysine (PLL) | 0-100 mg/mL | 2.5 mg/mL |
| | Chitosan(CHI) | 0-100 mg/mL | |
| | Polyethyleneimine (PEI) | 0-100 mg/mL | 0.05-10.0 mg/mL |
| | Polydiallyldimethylammonium chloride (PDAC) | 0-100 mg/mL | |
| | Polyallylamine hydrochloride (PAH) | 0-100 mg/mL | 5.0 mg/mL |
| Polyacrylic acid(PAA) | | 0-100 mg/mL | |
| Heparin (HEP) | | 0-100 mg/mL | |
| Alginate (ALG) | | 0-100 mg/mL | 2.5 mg/mL |
| Hyaluronic acid(HA) | | 0-100 mg/mL | |
| Polystyrene sulfonate(PSS) | | 0-100 mg/mL | |
| Poly-L-glutamic acid (PGA) | | 0-100 mg/mL | |
| Poly-DL-lactide-co-glycolide(PLGA) | | 0-100 mg/mL | |

The following Table 3 shows suitable cross-linking agents for use in certain embodiments of the invention to functionalize the PEM coating.

TABLE 3

Suitable Crosslinking
Suitable Crosslinking Agents/Techniques

| Method | Concentration Ranges | Preferred Concentration |
|---|---|---|
| carbodiimide 1-ethyl-3-(3-dimethylaminopropyl)carbodiimide (EDC) | 0-800 mM | 400 mM |
| N-hydrosulfosuccinimide (sulfo-NHS) | 0-200 mM | 100 mM |
| Glutaraldehyde | 0-10 mM | |

The physiochemical characteristics of the coated substrates fabricated in accordance with the invention may be evaluated by on known techniques and processes known in the art, such as ATR-FTIR, AFM, SEM and EDX.

Additional objects, advantages and novel features of the invention may become apparent to one of ordinary skill in the art based on the following examples, which are provided for illustrative purposes and are not intended to be limiting.

EXAMPLES

Example 1

Surface Treatments and Preparation of LbL Coatings on AZ31 Alloy with Natural Polymers Experimental—Creation of LbL Coatings with Natural Polymers AZ31 alloy was obtained from Alfa Aesar. The substrates were polished with 320, 600 and 1200 grit SiC paper, respectively, and cleaned under ultra-sonication using acetone. The polished substrates were soaked in 5 M NaOH solution at 60° C. for 2 hours, then thoroughly cleaned with de-ionized water and dried at 60° C. These hydroxide-treated AZ31 substrates were denoted as HAZ31. $MgF_2$ coatings on AZ31 were obtained by immersing cleaned substrates in HF (48-51 wt %, Acros Organics) at room temperature for 24 hours under constant stirring. The $MgF_2$ coated substrates (denoted as FAZ31) were first washed thoroughly with distilled water and then with acetone, and were dried in air at 50° C. for 20 minutes.

Polyethyleneimine (PEI) solution was prepared at a concentration of 0.05 mg/mL in HEPES (10 mM)-NaCl (150 mM) buffer, pH 7.4. Solutions of poly-L-lysine hydro bromide (PLL) and sodium alginate (ALG) were prepared at 2.5 mg/mL in HEPES-NaCl buffer. All solutions were sterile filtered through 0.22 μm filters before use. The NaOH treated (HAZ31) and $MgF_2$ coated (FAZ31) substrates were immersed in the PEI solution for 2 minutes to obtain a precursor layer with a stable positive charge to initiate the layer-by-layer (LbL) self-assembly process. Sequential layering of the polyelectrolyte coating and rinsing were done using dip coater (Desktop Dip Coater, MTI Corporation, USA, Model No EQ-HWTL-01-A). After 2-minute immersion, the PEI coated substrate was drawn at a speed of 200 μm/s. Polyelectrolyte multilayers were deposited by alternately dipping substrates in alginate (ALG) and poly-l-lysine (PLL) solutions for 1 minute, starting with ALG. They were subsequently washed in deionized water for one minute. Finally, five multilayer coatings, namely (ALG/PLL)$_5$-terminated with PLL were obtained and the coated samples were dried under room temperature conditions. LbL coated HAZ31 and FAZ31 ill be denoted as HAZ31L and FAZ31L, respectively. LbL coatings of (ALG/PLL)$_5$ were also performed on glass and titanium metal substrates following the procedure used for AZ31 substrates In order to immobilize fibronectin via chemical cross-linking, an additional ALG layer was coated on the five bilayered substrate, i.e. (ALG/PLL)$_5$. Cross-linking for protein immobilization was performed with a convention procedure. 1-Ethyl-3-[3-dimethylaminopropyl] carbodiimide hydrochloride ((EDC. 400 mM) in combination with N-hydroxysulfosuccinimide sodium salt (NHS, 100 mM) were used. The coupling chemistry is based on the reaction between the activated carboxylate groups of ALG with EDC and NHS that in turn facilitates the fibronectin immobilization via an amide bond formation. EDC and NHS were prepared separately in HEPES buffer of pH 7.4 and equal amounts of solutions mixed together immediately before use. The coated substrates having the alginate layer on the outer surface were immersed in EDC-NHS solutions for 4 hours at 4° C. following which they were rinsed with HEPES buffer and then with double distilled water for 2 minutes each. The HAZ31L and FAZ31L coatings treated with EDC-NHS and having NHS-ester activated sites were denoted as HAZ31LC and FAZ31LC.

To obtain the amide derivative by crosslinking the NHS-ester activated sites with amine group of PLL or fibronectin, the HAZ31LC and FAZ31LC coatings were treated with 2.5 mg/ml of PLL or 100 of fibronectin solutions in water for 45 min at room temperature, washed with buffer and dried. The PLL cross-linked HAZ31LC and FAZ31LC coatings were denoted as HAZ31LCP and FAZ31LCP, respectively. The fibronectin cross-linked HAZ31LC and FAZ31LC coatings were denoted as HAZ31LCF and FAZ31LCF, respectively. The EDC cross-linking and fibronectin immobilization were also performed on glass and titanium substrates containing ALG/PLL multilayer coatings.

Experimental: Characterization of LbL Coatings with Natural Polymers

Bare AZ31, hydroxide coated AZ31 (HAZ31) and fluoride coated AZ31 (FAZ31), HAZ31 and LbL coated (HAZ31L), HAZ31 LbL coated and EDC cross-linked and fibronectin immobilized (HAZ31LCF), FAZ31 and LbL coated (FAZ31L), and FAZ31LbL coated and EDC cross-linked and fibronectin immobilized (FAZ31LCF) substrates were analyzed using Attenuated Total Reflectance Fourier Transform Infrared Spectroscopy (ATR-FTIR, Nicolet 6700 Thermo Scientific). The spectra were collected in the range of from 4000 to 500 $cm^{-1}$. The surface morphology of the coatings was studied using scanning electron microscopy (SEM, Philips-XL30 FEG, Philips) operating at 10.0 kV. All the samples used for SEM analysis were coated with Pd using a sputter coater system. The chemical compositions of the films were studied by Energy Dispersive X-ray Spectroscopy (EDX, EDX Genesis, EDAX Inc.). The topography and surface roughness of the bare, LbL coated, cross-linked, and fibronectin immobilized AZ31 with hydroxide and fluoride treatments were characterized by non-contact oscillating Atomic Force Microscopy (AFM). AFM (MFP3D), Asylum Research) performed at room temperature in air at a scan speed of 1 Hz with a resolution of 512×512 pixels with silicon nitride conical tip of k=40 N/m (Mikromasch, Ltd), and RMS surface roughness analysis was performed.

Experimental: Cytocompatibility of LbL Coatings with Natural Polymers

Murine osteoblast cell line, MC3T3-E1, was obtained from ATCC (Manassas, Va.). Cells were cultured under 37° C. 5% $CO_2$, and 95% relative humidity in minimum essential medium alpha (MEM α, Gibco, Grand Island, N.Y.) or Dulbecco's Modification of Eagle's Medium (DMEM) containing 10% fetal bovine serum (FBS, Atlanta Biologicals, Lawrenceville, Ga.) and 1% penicillin streptomycin (P/S, Gibco, Grand Island, N.Y.). The supplier of the cell line (ATCC, Manassas, Va.) recommended the use of MEM α over DMEM and hence most of the cytocompatibility studies were performed using MEM α only. Cells at third to seventh passage were used in these experiments. Live/dead assays were performed to establish the viability of the cells. All the substrates were sterilized under UV for at least 2 hours. These sterilized substrates were placed in 12-well plates and cells were seeded on the substrates at a seeding density of 80,000 cells/well. One milliliter of media per square centimeter of surface area was used and the culture media was changed daily. The cells cultured on the experimental substrates for 1, 3, and 5 days were subjected to Live/Dead assay (Molecular Probes, Eugene, Oreg.), according to the instructions of the manufacturer. Briefly, cells were washed twice with phosphate buffered saline (PBS, Lonza Bio Whittaker, 1×, 0.0067 M (PO4) without calcium or magnesium) and were incubated in appropriate amounts of fluorescent dye for 45 minutes at room temperature. The cells were then rinsed twice using PBS and visualized using an inverted microscope with a fluorescence illuminator (CKX41, Olympus, Olympus America. Inc), and imaged with a digital camera (Olympus DP25 Microscope Camera, Olympus, Olympus America Inc). For each substrate, images were taken at least from three to six different locations to obtain an overview of the cell attachments (FIG. 1). Cells were fixed by using 2.5% glutaraldehyde and fixed samples were subjected to alcohol dehydration and coated with palladium in order to observe cell morphology by SEM. MC3T3-E1 pre osteoblast cell numbers were measured by using DNA quantification. The coated samples were placed in 12 well plates and cells were plated onto the samples at a seeding density of 80,000 cells/well and cultured for 3 days before changing, to differentiation media. Differentiation media was obtained by adding 50 μM ascorbic acid, 10 mM-glycophosphate, and 100 nM dexamethasone to alpha Minimum Essential Medium (MEM, Invitrogen). After 3, 7 and 14 days of culture with differentiation media, the cells were lysed and the DNA quantity was measured using Quant-iT PicoGreen dsDNA Reagent and Kits (Invitrogen) following manufacturer's instruction. The fluorescence of each sample was measured and analyzed at excitation ~480 nm, emission ~510 nm by Synerge2 microplate reader (Biotek). Intracellular Alkaline Phosphatase (ALP) activity was measured using para-nitrophenyl phosphate (p-NPP) (Sigma). After 3, 7 and 14 days of culture with differentiation media, cells were lysed and then incubated with p-NPP substrate for 1 hour at 37° C. to facilitate enzymatic activity of ALP. The enzymatic reaction was stopped by adding 0.3 N NaOH solution and the ALP activity was calculated by measuring the para-nitrophenol (p-NP) absorbance at 405 nm using Synergy2 (Biotech) microplate reader. A standard curve was made with p-NP known concentration by diluting different concentration with 0.02 N NaOH. The cleaved p-NP level from p-NPP was normalized with total protein concentration. The total protein was measured by using Bicinchoninic acid, BCA protein kit (Thermo scientific) following manufacture's instruction.

Experimental: Stability, in vitro Degradation and Corrosion Resistance of LbL Coatings with Natural Polymers In order to verify the stability of the LbL films Dulbecco's Modification of Eagle's Medium (DMEM) with 10% Fetal Bovine Serum (FBS) and 1% PSS was used. The samples were immersed in media for two weeks and the media was changed and refreshed every 24 h. After the immersion at various time points, the surface morphology and chemical changes of the coated samples were analyzed using SEM and FTIR.

The in vitro degradation characteristics of the bare, LbL coated and cross-linked substrates were tested in DMEM) with 10% Fetal Bovine Serum (FBS) and 1% P/S was used. The coated substrates were sterilized by UV light exposure for at least 30 min per side. In order to determine the pH and magnesium ion concentration, each coated substrate were placed inside tissue culture 12 well plates and was completely immersed in 2.0 ml of DMEM media. The immersed samples were kept at 37° C., 5% $CO_2$ and 95% relative humidity for 21 days. The media was changed and replaced with fresh media after each 24 h to monitor the degradation rate under in vitro conditions. For each coating groups (i.e. AZ31, HAZ31, HAZ31L, HAZ31LCF, FAZ31, FAZ31L and FAZ31LCF), three samples were used. The pH of the extracted media was measured (350, Beckman (Coulter) and was stored at 4° C. for Mg ion concentration analysis. The collected media was diluted with 0.03 M tris buffer, before they were used for Mg ion concentration analysis using Inductively Coupled Plasma (ICP, iCAP 6000 series, Thermo Electron Corporation). Each ICP sample was measured in triplicate. Electrochemical characterization studies were performed using CHI 604A (CH Instruments, Inc., Austin, Tex.) work station. A three electrode cell set-up was used wherein the prepared coated Mg alloy samples, Ag/AgCl and a platinum wire were used as the working, reference and counter electrodes respectively. The electrolyte used to simulate the in-vitro conditions consisted of DMEM with 10% FBS and 1% P/S. Electrochemical tests of some of the samples were also performed using MEM-α with 10% FBS and 1% P/S. Testing was performed at 37° C. Preparation of working electrode involved the use of silver epoxy to provide contact between the Mg alloy substrate and a copper wire following which the region of contact was insulated using a non-conducting epoxy resin such that only one face of the alloy surface was exposed to media. Electrochemical impedance spectroscopy (EIS) studies were carried out at open circuit potential for 10 mV sinusoidal amplitude over a frequency range of 100 KHz to 0.01 Hz. A stable open circuit potential was established prior testing. The evolution of hydrogen was tested by placing the substrates in Hank's balance salt solution (HBBS, Sigma Aldrich, H-1387) at 37° C. under an inverted funnel connected to a graduated burette and measuring the burette water level intermittently for 10 days. Samples were measured for length and width, then sterilized under UV radiation, one hour each side. Samples were then placed in mesh plastic bags and suspended within the Hank's solution to allow for full surface exposure. Three samples were placed for each condition to account for the low hydrogen evolution anticipated from the coated samples. The ratio of substrate surface area to Hanks balanced salt solution (HBSS) volume was kept constant at 10 cm$^2$ L$^{-1}$.

Experimental: BSA Release from LbL Coatings with Natural Polymers

Figure 2:
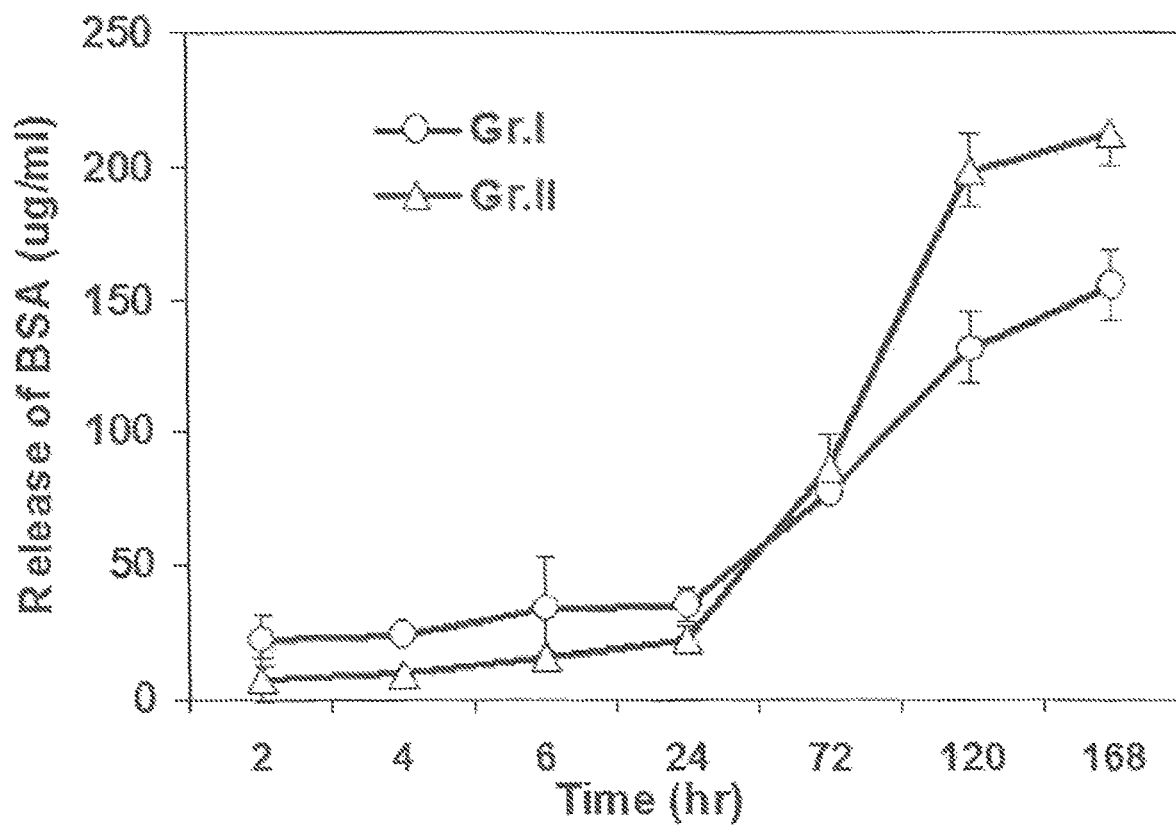
FIG. 2 is a plot showing the release profile of BSA from LbL coated substrates in Hanks balance salt solution for two samples, in accordance with certain embodiments of the invention.

Two groups of BSA loaded multi-layered coatings were fabricated by the LbL process. In group 1, BSA was incorporated in the final five layers (ALG/PLL)$_5$+ (BSA/PLL)$_5$. In group 2, LbL coated and cross linked substrates were suspended in BSA solution and allowed to adsorb overnight at 4° C. For the BSA release experiments, two groups of BSA incorporated substrates were put in 2 mL of Hanks solution. At a series of different time points 2 mL of the supernatant was collected and replaced by 2 mL of fresh Hanks solution. A micro-BCA Protein Assay Kit (Pierce Biotechnology, Rockford Ill.) was used to detect the total amount of protein released during a time point (FIG. 2).

Results: Characterizations of LbL Coatings with Natural Polymers

The FTIR of bare, surface treated AZ31 with NaOH (HAZ31) and HF (FAZ31) were generated. The spectrum collected on the bare substrate showed no peaks. The most predominant spectral feature with NaOH treatment was the intense sharp peak observed at 3693 cm$^{-1}$. In contrast, magnesium fluoride had only one peak below 600 cm$^{-1}$ which was due to the presence of magnesium fluoride or magnesium oxides-fluorides. The FTIR spectrum of sodium alginate, poly-l-lysine and polyethylenimine was generated; the polyelectrolytes used for the LbL coatings on AZ31. The FTIR spectra of all these polyelectrolytes showed their distinct peaks, which are characteristic of their main functional moieties such as carboxyl and amino groups. FTIR spectrum was generated for ALG-PLL coated HAZ31 (i.e. HAZ31L), ALG-PLL coated FAZ11 (i.e. FAZ31L), ALG-PLL coated and cross-linked and fibronectin immobilized HAZ31 (HAZ31LCF), ALG-PLL coated cross-linked and fibronectin immobilized FAZ31 substrates (FAZ31LCF). The HAZ31L and FAZ31L substrates showed peaks similar to that of polyelectrolyte used and the intensities of these polyelectrolyte's peaks increase expectedly with increase in number layers in the coating. It was observed that all of the former peaks for the major functional groups are not significantly changed after cross-linking. The surface morphologies of the coated and cross-linked samples HAZ31, HAZ31L, HAZ31LCF, FAZ31, FAZ31L, FAZ31LCF were examined using SEM. The initial alkaline treated and fluoride coated substrates showed the formation of a protective film mimicking the surface morphology of the bare AZ31. The SEM images of HAZ31L demonstrated the formation of a homogenous polyelectrolyte coating on bare AZ31L surfaces. The SEM images also showed that the alkaline treated alloy with LbL coatings (HAZ31L) appeared to form a homogenous surface coating, and fluoride coated alloys (FAZ31L) showed formation of a dense and smooth surface. The SEM images of the EDC cross-linked and fibronectin immobilized HAZ31LCF and FAZ31LCF substrates, demonstrated that the film microstructure and morphology were not changed much after cross-linking. The AFM topographic images of surface pretreated, LbL coated, LbL coated and cross-linked substrates were generated. The images demonstrated a significant difference between the surface treated, LbL coated and EDC cross-linked and fibronectin immobilized AZ31. The surface roughness (RMS) value obtained for bare AZ31 was 111 nm. After the alkaline and fluoride pretreatments the surface roughness slightly decreased to 97 and 95 nm, respectively. The surface roughness values were decreased after LBL coatings on both HAZ31 and FAZ31 (88 and 78 nm), however, these values slightly increased after cross-linking with EDC-NHS to 93 and 86 nm for HAZ31LC and FAZ31LC, respectively. The surface roughness values were decreased to 63 nm for both the HAZ31LC and FAZ31LC samples after the EDC cross-linking and fibronectin immobilization.

Results: Cytocompatibility of LbL Coatings with Natural Polymers

In order to determine the cytocompatibility and cell adhesion capability of these LbL coatings, MC3T3 cells were grown and cultured for 1 and 5 days on bare AZ31, HAZ31, FAZ31, HAZ31LC, HAZ31LCF, FAZ31L, FAZ31LC, FAZ31LCP and FAZ31LCF, were studied using fluorescence microscopy, the results of which are shown in FIG. 1. There are only few cells that were found to attach on bare AZ31, HAZ31, and HAZ31LC. The cells also did not attach and proliferate even after 5 days of cell culture on bare AZ31 (FIG. 1*a*) or on HAZ31, and HAZ31L. Although the fluoride coated AZ31 showed considerable cell attachments, only few cells attached to FAZ31L. The live-dead cell attachment studies on these cross-linked and fibronectin immobilized films are also shown in FIG. 1 for 1 and 5 days of cell culture, respectively. The results clearly demonstrated that while the cells are attached and alive on the cross-linked PLL and fibronectin immobilized LbL coated cover glass and FAZ31, there are only few live cells on the HAZ31LCF or on HAZ31LCP. Although the cells initially attach to the HAZ31LCP or HAZ31LCF, the number of dead cells appeared to have increased with time and there were hardly any live cells observed at day 3 or at day 5. The DNA contents of osteoblasts cultured on the bare AZ31, titanium foil and FAZ31LCF were generated. The DNA content was measured with fluorescence assay. For FAZ31LCF and Ti, initial cell attachments were much higher compared to bare AZ31. The cells which attached and proliferated rapidly between 7 and 14 days resulted in an increase in DNA concentration for all the samples. Furthermore, the amount of cell attached to the LbL coated sample (FAZ31LCF) was still much higher than bare AZ31 and comparable to biologically inert Ti metal. Alkaline phosphatase (ALP) activity is one of the most widely used markers for early osteoblastic differentiation. The ALP activity of osteoblasts cultured on the bare magnesium AZ31, pure titanium foil (denoted as Ti) as control and LbL coated and cross-linked FAZ31LCF were generated. The osteoblast adhered to titanium and FAZ31LCF displayed a higher ALP expression compared to the bare AZ31 substrates. The LbL coated cross-linked and fibronectin immobilized FAZ31 and titanium substrate possessed a stronger ability for cell differentiation.

Results: Stability, in vitro Degradation and Corrosion Resistance of LbL Coatings with Natural Polymers The FTIR spectra of cross-linked and fibronectin immobilized LbL coated HAZ31 and FAZ31 immersed and aged in media for 7 and 14 days, respectively, was generated. The FTIR bands present in these aged samples were very similar to the peaks of the as LbL coated sample with slight variation in the peak positions, which confirmed that the multilayered films were still present on the surfaces of the HAZ31 and FAZ31. The SEM images of HAZ31LCF aged for 7 and 14 days were generated. The FUR results also clearly showed the presence of alginate and poly-l-lysine after 14 days of aging. Absence of any apparent cracks even after 14 days of immersion in media on the surface of the FAZ31 indicated that the LbL coated FAZ31 substrates were more corrosion resistant than HAZ31L. No significant differences were observed in the FTIR and SEM data between the aged FAZ31L and aged FAZ31LCF samples, indicating that the LbL coated and cross-linked and fibronectin immobilized films possess very similar in vitro stability.

The changes of $Mg^{2+}$ concentrations value of the soaking medium over time during non-static immersion tests were observed. ICP-OES analyses showed a rapid release of $Mg^{2+}$ ion for AZ31 and HAZ31 compared to FAZ31. FAZ31 showed a sustained release of $Mg^{2+}$ ions during the entire duration of the experiment. The amount of $Mg^{2+}$ released from fluoride coated substrates (FAZ31) was much lower than magnesium released from bare and alkaline treated AZ31. Similar trends were observed in LbL coated, cross-linked and fibronectin immobilized LbL coated substrates following both alkaline and fluoride treatments. These results clearly demonstrated that all the fluoride coated substrates were more corrosion resistant. The pH change in the DMEM media containing the bare substrate, LbL coated and fibronectin immobilized cross-linked substrates was observed. It was seen that the pH values of all the samples were in the alkaline region but the fluoride coated substrates were less alkaline compared to bare and hydroxide coated AZ31. The Nyquist plots of the coatings on HAZ31 and FAZ31, respectively, were generated. The data obtained for bare AZ31 alloy was also inserted for comparison. Alkaline treatment showed an increase in the semi-circle diameter (~4026Ω), which was representative of the resistance to charge transfer occurring at the interface of the alloy and DMEM solution, from that of bare substrate (~1890Ω). Further addition of LbL coatings increased the charge transfer as indicated by the lower resistance (~3378Ω), a trend that remained, following the cross-linking step (~3347Ω). In the case of fluoride pretreatment-FAZ31, a 30 fold increase in resistance (~60468Ω) was observed, indicative of the formation of a protective fluoride film that acts as a barrier to AZ31 (~1890Ω) corrosion. However, similar to alkaline treatment, the samples with fluoride pretreatment showed an increase in charge transfer following LbL (25539Ω) and cross-linking steps (8065Ω). The hydrogen evolution studies in Hank's solution were performed only on the fluoride coated samples, i.e. FAZ31, FAZ31L and FAZ31LCF along with the bare AZ31 substrates. The bare AZ31 substrate as expected showed a quick and copious amount of cumulative hydrogen evolution with time and the rate of hydrogen release decreases slightly with immersion time. On the other hand, FAZ31, FAZ31L and FAZ31LCF substrates only showed some hydrogen release at the beginning of the study but there were hardly any hydrogen release observed after few days from the commencement of the experiment. The cumulative volume of hydrogen released from these different substrates follow the order FAZ31<FAZ31L<FAZ31LCF<AZ31.

Results: BSA Release from LbL Coatings with Natural Polymers

The BSA release studies in Hank's balance salt were performed only on the fluoride coated samples, and the results were shown in FIG. 2. Group 1 included the FAZ31L substrates with the addition of another 5 layers of BSA/PLL, Group II includes FAZ31LC with 12 hrs of BSA on the top of the surface. The results shows that BSA incorporated in both groups of substrates exhibited an initial sustained release for 24 hrs and followed by burst release for longer period.

Example 2

Surface Treatments and Preparation of LbL Coatings on AZ31 Alloy with Synthetic Polymers Experimental—Creation of LbL Coatings with Synthetic Polymers Hot rolled AZ31 alloy was acquired from Alfa Aesar (Ward Hill, Mass., USA) and was used without further thermal or mechanical treatment. Samples were cut into 1.25×1.25×0.08 cm pieces and cleaned by etching in 3% nitric acid solution in ethanol. Samples were then polished to 1200 grit (5 μm) using SiC polishing paper and sonicated for 30 minutes in acetone. Following sonication, samples were incubated in a 5M NaOH solution for 2 hours at 60° C. to form an $Mg(OH)_2$ surface layer, then dried in air at 60° C. for 1 hour. Samples were subsequently rinsed in deionized water for 5 minutes, then again dried at 60° C. for 30 minutes. Layer-by-layer coatings were created via a dip-coating method (Desktop Dip Coater, Model No EQ-HWTL-01-A, MTI Corporation, USA), wherein for each coating the substrates were dipped into the polymer solution, incubated for 1 minute, withdrawn at 200 μm/s and dried in air. Layers were generated with the following sequence, "ABCBCBCBCB". Solutions A and C contain cationic polymers, polyethylenimine (PEI, MW 25,000) at 10 mg/ml in DI water and poly(allylamine hydrochloride) (PAH, MW 58,000) at 5 mg/ml in 4-(2-Hydroxyethyl)piperazine-1-ethanesulfonic acid buffer (HEPES buffer), respectively. Solution B consists of a synthetic anionic polymer, 50:50 poly(lactide-co-glycolide) (PLGA 50:50, MW 30,000-60,000) 75:25 poly(lactide-co-glycolide) (PLGA75:25, MW 76,000-115,000) or polycaprolactone (PCL, MW 70,000-90,000) each at 50 mg/ml in dichloromethane. All five polymers were acquired from Sigma-Aldrich. Three different variations of layer-by-layer coatings were generated, depending on the anionic polymer used, subsequently termed PLGA50:50, PLGA75:25 or PCL depending on the anionic polymer utilized for the 'B' layer.

Experimental: Characterization of LbL Coatings with Synthetic Polymers

The formation of the $Mg(OH)_2$ layer was confirmed utilizing glancing angle x-ray diffraction (GA-XRD, Philips PWI830 Diffractometer) using copper Kα radiation with a 2θ range of 10-80°, 0.02° step size and an ω angle of 1° offset. The chemical nature of the coatings was confirmed by Attenuated Total Reflectance Fourier Transform Infrared spectroscopy (ATR-FTIR, Nicolet 6700 spectrophotometer, Thermo Electron Corporation) using a diamond ATR Smart orbit. Spectra were obtained at 1.0 $cm^{-1}$ resolution averaging 64 scans in the 400-2500 $cm^{-1}$ frequency range. The surface morphology of the coating was studied using scanning electron microscopy (SEM, Joel JSM-6610LV) at 10 kV operating voltage. Prior to imaging samples were sputter coated with palladium (Cressington sputter coater 108A).

Experimental: Cytocompatibility of LbL Coatings with Synthetic Polymers

Murine MC3T3-E1 pre-osteoblast cells (ATCC, Manassas, Va.) and Human Mesenchymal Stem Cells (hMSC, Lonza USA) were utilized for cell culture studies. Cells were cultured in minimum essential medium alpha (α-MEM, Gibco, Grand Island, N.Y.) containing 1% penicillin/streptomycin antibiotics (P/S, Gibco. Grand Island, N.Y.) and either 10% fetal bovine serum for MC3T3, or 20% fetal bovine serum, for hMSC (FBS, Atlanta Biologicals, Lawerenceville, Ga.) at 37° C., 5% and 95% relative humidity. Substrates were placed in 12-well plates and sterilized rising UV radiation for 40 minutes on each side. The substrates were then seeded with cells with a total media volume of 2 ml/well. Media was changed every other day throughout the testing period.

Figure 3:
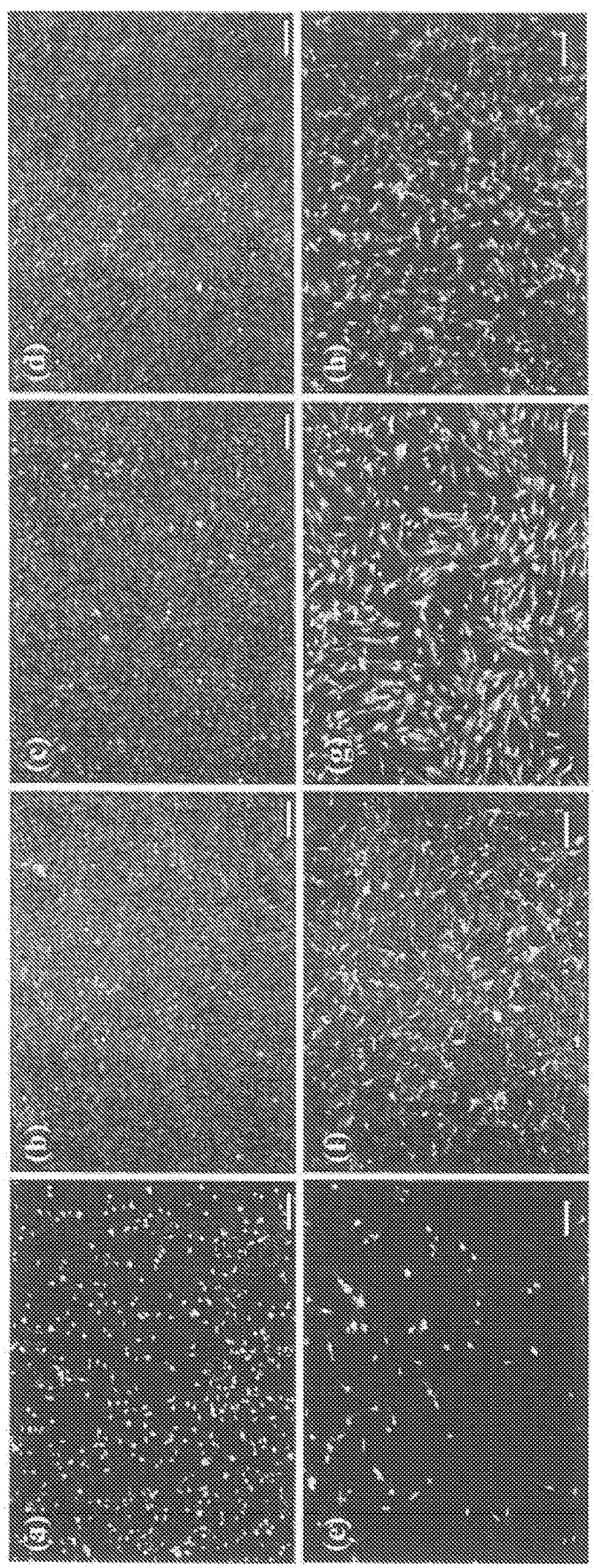
FIG. 3 including views (a) through (h) shows live/dead staining of MC3T3 osteoblasts ((a) through (d)) and hMSCs ((e) through (h)) on Day 3 of culture post seeding on uncoated AZ31 ((a) and (e)), PCL ((b) and (f)), PLGA 50:50 ((c) and (g)) and PLGA 75:25 ((d) and (h)) indicating improved biocompatibility of coated substrates compared to uncoated substrates, in accordance with certain embodiments of the invention.

Cell viability was assessed using Live/Dead staining (Invitrogen, Live/Dead Staining Kit). MC3T3 and hMSC cells were seeded at a density of 70,000 cells/well onto substrates. The assays were performed 3 days post-seeding. The coated alloy substrates were rinsed with phosphate buffered saline (PBS, Lonza BioWhittaker Buffers and Buffered Salines, 1×, 0.0067M($PO_4$)) without calcium or magnesium) and then incubated for 30 minutes in live/dead stain, calcein AM and ethidium homodimer-1, diluted in PBS according to manufacturer's instructions. After incubation, the samples were again washed with PBS and then imaged using fluorescence microscopy (Olympus CKX41, Olympus DP25 Microscope Camera) (FIG. 3).

Figure 4:
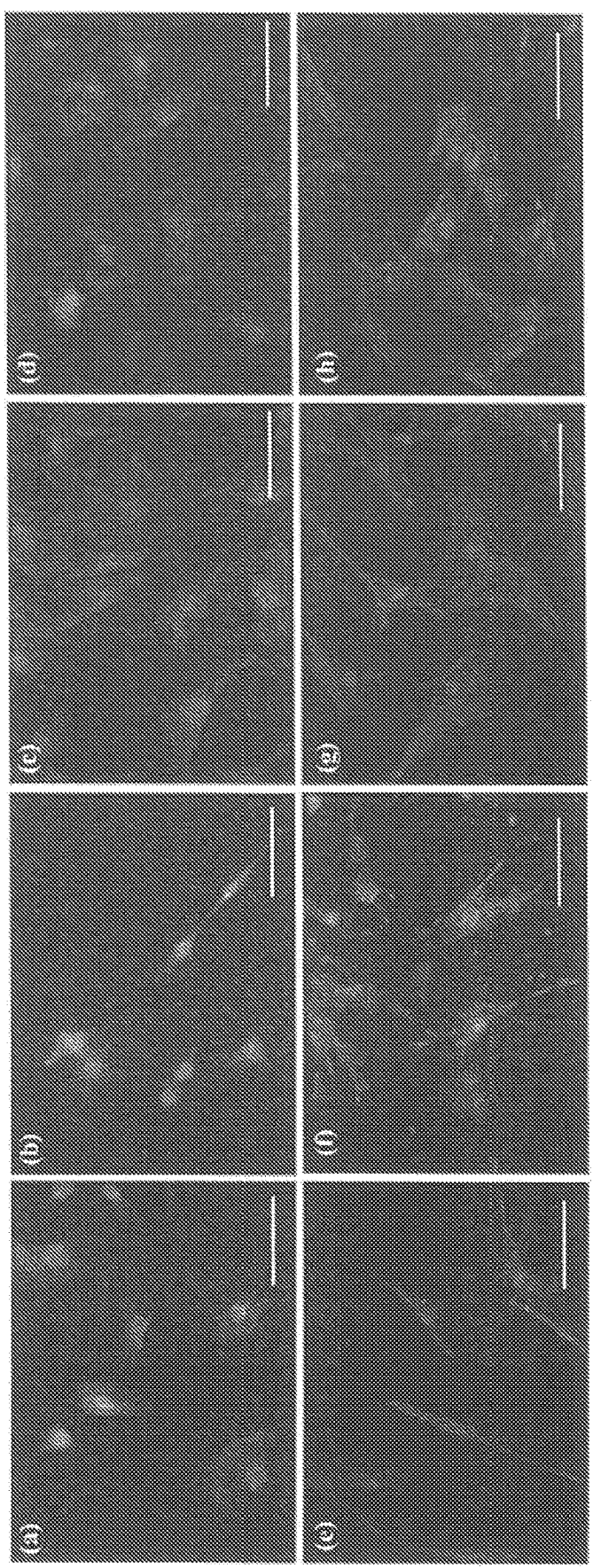
FIG. 4 including views (a) through (h) shows cell morphology of MC3T3 osteoblasts ((a) through (d)) and hMSCs ((e) through (h)) observed at 24 hours post seeding through actin-nucleus co-staining, on uncoated AZ31 ((a) and (e)), PCL ((b) and (f)). PLGA 50:50 ((c) and (g)) and PLGA 75:25 ((d) and (h)), in accordance with certain embodiments of the invention.

Cellular adhesion and morphology was observed using actin and nucleus staining. MC3T3 and hMSC cells were seeded on sterilized substrates at a concentration of 20,000 cells/ml and cultured in appropriate media for 24 hours. Cells were then rinsed with PBS, fixed using a 4% paraformaldehyde solution then permeabilized with a 0.2% Tween20 solution (Bio-Rad, USA). Following this cellular actin was stained using phalloidin (Sigma Aldrich) and nuclei were stained using dapi (Applichem) according to manufacturer's instructions. Cells were imaged using fluorescence microscopy (FIG. 4). Following fluorescence imaging, fixed samples were then subjected to alcohol dehydration and mounted for SEM imaging. Samples were coated with palladium (Cressington sputter coater 108A) in order to image the cell morphology using scanning electron microscopy.

Figure 5:
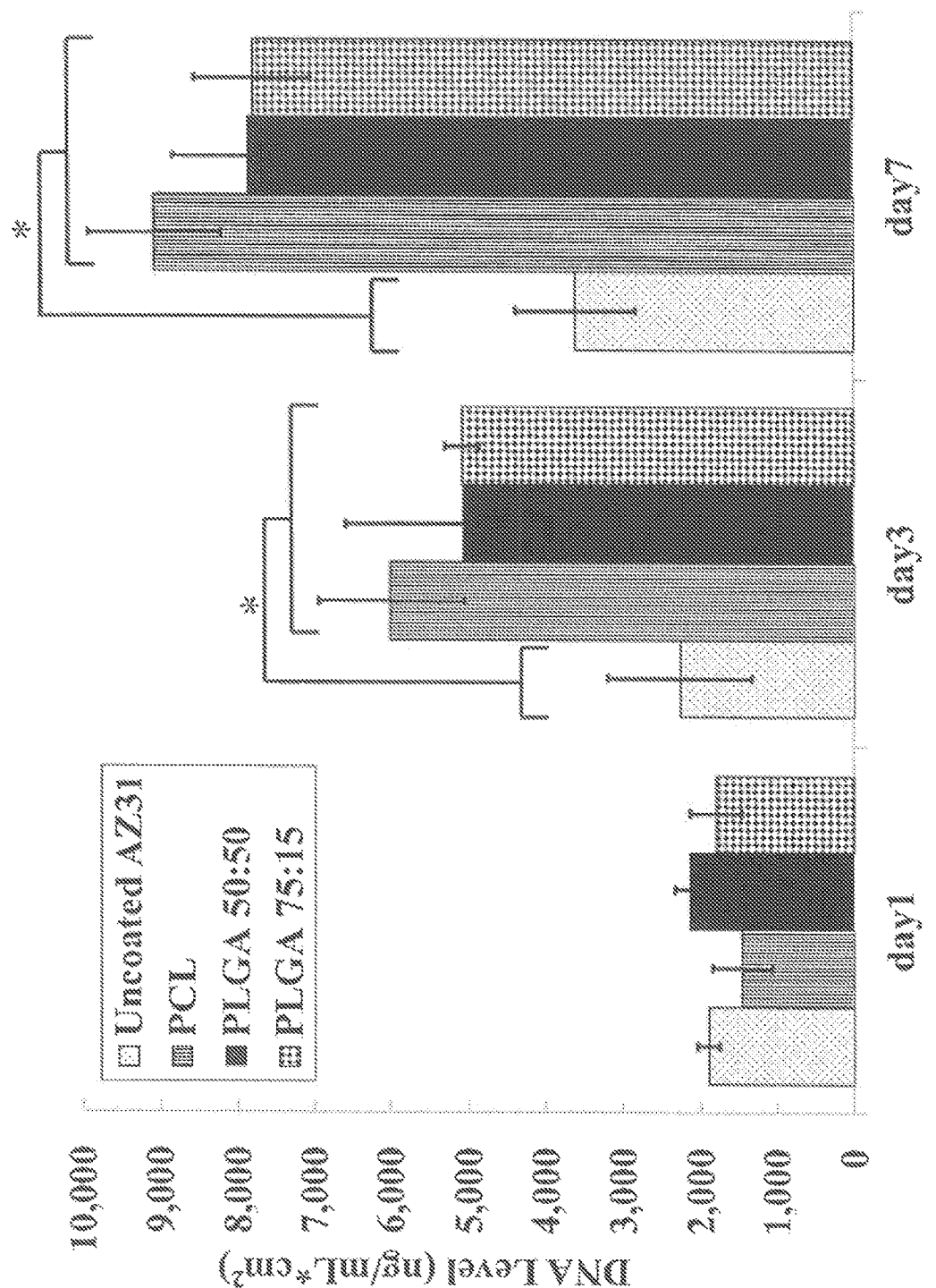
FIG. 5 is a bar graph showing quantification of total DNA content, using MC3T3 osteoblasts on substrates at various time points for uncoated and coated substrates, in accordance with certain embodiments of the invention.

Quantification of cellular DNA levels as a measure of proliferation was assessed with MC3T3 cells. Cells were seeded at a density of 80,000 cells/ml and cultured for 1, 3 and 7 days. Substrates were rinsed with PBS then cells were lysed (CellLytic, Sigma Aldrich). The Quan-It PicoGreen dsDNA Reagent and Kit (Invitrogen) was used to measure cellular DNA according to manufacturer's instruction. Lamda dsDNA was used for the standard curve and the fluorescence level was measured using Synerge2 Multi-Mode Microplate Reader (Biotek, USA). Statistically significant differences were assessed through ANOVA with Dunnett's 1-tailed t-test post-hoc testing, assuming AZ31 control values to be lower than coated substrates. Significance was set at the $p<0.05$ level. IBM-SPSS statistical analysis software was used for calculations (FIG. 5).

Experimental: In vitro Degradation and Corrosion Resistance of LbL Coatings with Synthetic Polymers Electrochemical corrosion characterization of the coated alloy samples was performed using a CH604A (CH Instruments Inc) electrochemical work station. Following sample preparation as described previously, length and width were measured and then one side of each sample was connected to a wire with silver epoxy and then electrically insulated with polymeric epoxy, such that only one side is exposed for electrochemical testing. Ag/AgCl and a platinum wire were employed as the reference and counter electrodes, respectively. Testing was carried out utilizing a 3-neck jacketed flask (ACE Glassware) filled with 125 mL Dulbecco's Modified Eagle's Medium (DMEM) containing 10% fetal bovine serum (P/S, Atlanta Biologicals, Lawerenceville, Ga.) and 1% penicillin/streptomycin antibiotics (P/S, Gibco, Grand Island, N.Y.), equilibrated to 37° C. All the specimens were allowed to equilibrate to reach a stable open circuit potential (OCP), before initiating the potentiostatic polarization tests at a scan rate of 1.0 mV/s. The corrosion current was determined using the Tafel extrapolation of the polarization curve and normalized by the exposed surface area to yield a measurement of corrosion current density. The Tafel extrapolation was taken at potential values 50 mV below and above the corrosion potential value to ensure proper extrapolation. The software program Origin with a Tafel extrapolation packet was used to perform the analysis and plot the data.

Corrosion profile up to 7 days was assessed by analyzing the magnesium ion concentration in media extracted after sample incubation. The coated substrates were sterilized by UV light exposure for 1 hour per side. Each substrate was then soaked in 2 mL of DMEM containing 10% FBS and 1% P/S under standard growth conditions of 37° C., 5% CO) and 95% relative humidity for 7 days. The media was changed and collected every 24 hours to monitor the dissolution rate under in vitro conditions. The collected media was diluted in 0.03 M Tris buffer solution and analyzed using inductively coupled plasma optical emission spectroscopy (ICP-OES, iCAP duo 6500 Thermo Fisher). Magnesium ion concentrations in solution were compared to media and uncoated substrate controls. Samples were prepared in triplicate for each condition. Statistically significance differences were assessed daily through ANOVA with Dunnett's 1-tailed t-test post-hoc testing, assuming AZ31 control values to be higher than coated substrates. Significance was set at the $p<0.05$ level. IBM-SPSS statistical analysis software was used for calculations.

The evolution of hydrogen was tested by placing the substrates in Hank's solution (Sigma Aldrich) at 37° C. and measuring the evolved hydrogen over a two week time span. Sample dimensions were recorded prior to sterilizing under UV radiation, 1 hour each side. Samples were placed in individual mesh bags and suspended within 1 liter beakers of Flank's solution, underneath an inverted funnel. A burette was placed over-top of the funnel above the samples to capture hydrogen released. Three samples were suspended for each condition to account for the low hydrogen evolution anticipated from the coated samples. To the greatest extent possible, difficulties and concerns associated with measurement of hydrogen evolution have been addressed. All beakers, funnels and burettes are glass so as to prevent hydrogen permeation. The samples were suspended to ensure full surface exposure and the inverted funnels were elevated to prevent ion accumulation within the funnel volume. Solution level in each burette was measured intermittently for two weeks. The coatings were characterized post-corrosion using a scanning electron microscopy.

Results: Characterizations of LbL Coatings with Synthetic Polymers

Glancing angle x-ray diffraction (GA-XRD) was used to confirm the formation of the $Mg(OH)_2$ layer on the surface of the AZ31 substrates. Following sodium hydroxide treatment and rinsing in DI water, the substrate was dried and kept in a desiccator until the diffraction measurement was completed. GA-XRD spectra was collected along with simulated spectra for pure magnesium and magnesium hydroxide. The collected spectra showed minor peaks associated with major peaks of $Mg(OH)_2$ spectra, particularly at approximately 18.5 and 38° 2θ angles.

FT-IR was used to follow the development of the layer-by-layer coatings on the AZ31 substrates. The FT-IR spectrum of the PCL (i), PLGA 50:50 (ii) and PLGA 75:25 (iii) coated samples after all five cationic/anionic layer pairs were applied, respectively. Further FT-IR testing of individual layer assembly showed small peaks of cationic polymers when these polymers were the top coat. For each coating type, the coated substrate was compared to FTIR spectra of $Mg(OH)_2$-treated substrate and pure spectra of each utilized polymer component. The characteristic bonds at numerous wave numbers, especially the C=O stretching at 1750 cm-1 and the numerous C—O—C and C—H bending peaks between near 1080 cm-1 and 1500 cm-1, were indicative of the presence of the PCL and PLGA polymers, Additionally, there were minor peaks around 1625 cm-1 visible which matched the pattern for PAH and were likely associated with C=C bonds of unreacted ends of the PAH chains. No carbon or nitrogen-based peaks were seen on the bare metal substrates devoid of the polymer, though the peak at around 3600 cm-1 was associated with free —OH bonds. The coated substrate spectra were alter completing the coating process and the presence of the thicker, top-coating anionic polymers (PCL. PLGA 50:50 and PLGA 75:25) masked most bond peaks characteristic of the cationic PEI and PAH polymers.

Scanning electron microscopy was used to observe the morphology of the substrates after the coating process. Images of the substrates as-polished (a) and after layer-by-layer coatings (b-d) were produced. The as-prepared AZ31 substrate showed a flat but imperfect surface with grooves remaining from the final 5 µm polishing paper. The sodium hydroxide-treated surface displayed slightly altered morphology of the substrate, reducing the visibility of residual grooves from polishing. The PCL (b), PGLA 50:50 (c) and PLGA 75:25 (d) layer-by-layer coated substrates showed smoother, muted surfaces with only slight remnants of the polishing artifacts remaining. The coatings were non-porous and did not show any signs of delamination from the alloy surface. Qualitatively, this reinforced the confirmation of the successful $Mg(OH)_2$ treatment and anionic-cationic layer-by-layer assembly to the surface of AZ31 substrates.

Results: Cytocompatibility of LbL Coatings with Synthetic Polymers

Live/Dead staining of osteoblasts and hMSCs 3 days post seeding were conducted. For both MC3T3 and hMSC cell cultures, live/dead staining indicated improved cell viability and proliferation on coated substrates over the uncoated AZ31 alloy (FIG. 3). No discernible difference was seen between the three types of polymer coatings. Actin staining of osteoblasts and hMSCs 24 hours post seeding were conducted. For MC3T3 cells, cellular morphology was circular and poorly defined on the uncoated AZ31, without strong actin fiber staining, indicating that the cells were likely poorly adhered to the substrate (FIG. 4). On the PCL-coated substrate, cells appeared elongated while on the PLGA 50:50 and PLGA 75:25 coated substrate cells appeared well spread out showing strong actin filaments extended in numerous directions (FIG. 4). For hSMCs, cells cultured on uncoated AZ31 appeared extremely elongated, though better adhered than the MC3T3s under the same conditions. On the PCL coated substrates, hMSCs appeared somewhat elongated, but less than the MC3T3s did under the same condition. The hMSCs grown on the PLGA 50:50 (g) and PLGA 75:25 (h) coated substrates appeared very healthy and well adhered with strong actin fibers extending in various directions on the substrates.

The same substrates from the cell morphology study, dehydrated and mounted for electron microscopy examination, allowed for simultaneous observation of the coatings, the cells and the interaction between the two. Fixed MC3T3 cells were barely visible on the corroded AZ31 substrate. Morphologies of MC3T3s on the polymeric coatings were similar to those observed through actin staining: the cells grown on the PCL coated substrate appeared more elongated while the cells grown on the PGLA 50:50(c) and PLGA 75:25 (d) substrates appeared more spread out. The cells on PCL substrates did not appear to be as fully adhered as those on the PLGA substrates, with some portions of the cytoskeleton rising up above the surface of the polymer. SEM images of hMSCs fixed on the coated and uncoated substrates showed similar trends. Cells on the uncoated AZ31 were thin and very elongated, cells on the PCL were also elongated but to a lesser extent while cells on PLGA 50:50 (g) and PLGA 75:25 (h) were spread out and well adhered to the substrates.

The quantification of total DNA content from MC3T3 cells was generated. Grown over the period of 1, 3 and 7 days, DNA quantification studies supported what was seen qualitatively in the live/dead staining, that the cell viability and proliferation was higher on the coated substrates in comparison to the uncoated substrate. Although there was no statistical difference after day 1, days 3 and 7 samples coated with PCL, PLGA 50:50 and PLGA 75:25 showed significantly higher DNA levels than the uncoated substrates. High DNA levels were correlated with higher numbers of cells on the substrates (FIG. 5).

Results: In vitro Degradation and Corrosion Resistance of LbL coatings with Synthetic Polymers Polarization curves for the uncoated and coated substrates were generated. The corrosion potential and corrosion current densities were calculated from extrapolation of the Tafel plots. All three coatings, PCL, PLGA 50:50 and PLGA 75:25 on the substrates resulted in an $E_{corr}$ that was more anodic than the uncoated AZ31 alloy indicating that the coatings did provide a barrier for corrosion. PLGA 75:25 offered the greatest improvement in corrosion potential, followed by PCL and PLGA 50:50 which were quite similar. Additionally, the presence of the polymer coatings on AZ31 lowered the $i_{corr}$ values compared to the uncoated AZ31 alloy substrate. PCL offered the greatest reduction in corrosion current, followed by PLGA 50:50 and PLGA 75:25, which were quite similar. Both PGLA 50:50 and PLGA 75:25 showed a breakdown in the anodic corrosion current at lower potential values.

Daily released magnesium ion concentration in media for coated and uncoated substrates can be seen FIGS. 1a-f. This data shows the dissolution profile as a function of soluble magnesium ion release over a one week period under in vitro culture conditions. Although connected more directly with passivation coating dissolution, or here $Mg(OH)_2$ dissolution, than magnesium corrosion, the localized ion concentrations are an important consideration for biocompatibility of the substrate. At each time point the magnesium level in media for coated samples is significantly lower ($p<0.05$) than the uncoated AZ31 substrates. Though not calculated, it appears that magnesium ion levels of coated substrates remaining higher than basal media levels for all time points. This indicates that the coatings provide some corrosion protection but do not fully passivate the substrate from corrosion.

Cumulative hydrogen gas evolution plots for the uncoated and coated substrates were generated. Measurements indicated that cumulative hydrogen released from uncoated AZ31 was much higher than that of coated substrates. Uncoated AZ31 showed a characteristically high corrosion rate initially, through about the first 12 hours, followed by slower, relatively constant corrosion rate through the remaining period of the study. All coated substrates showed a slow rate of hydrogen release initially, through the first 48 hours of testing. The corrosion then plateaued, showing no additional measurable release after this 48 hour period. The SEM images of samples post corrosion in Flanks solution. Electron microscopy of these samples at the end of the corrosion period showed the presence of surface cracks on the uncoated AZ31, characteristic of magnesium corrosion morphology. The polymer-coated substrates showed various levels of corrosion progression. PLGA 50:50 showed the most aggressive progression of corrosion, with cracking morphology similar to the uncoated substrate and nearly no visible polymer remaining. PLGA 7:525 showed some underlying cracking beginning to form, with the bulk of the sample still coated in polymer. PCL showed the least amount of corrosion, displaying some defects in the polymer coating but no visible cracking morphology.

The invention claimed is:

1. A coated medical implant device, comprising:
   a biodegradable magnesium-based substrate;
   a pretreatment agent selected from the group consisting of alkali metal hydroxide, hydrogen fluoride and combinations thereof, applied to a surface of the biodegradable magnesium-based substrate to form a charged substrate having a positive charge or a negative charge;
   a polyelectrolyte multilayer coating deposited on the charged substrate, comprising:
      a plurality of interfacing, individual polymer layers, comprising:
         one or more synthetic polymer layers comprising poly-L-lysine having a positive charge; and
         one or more natural polymer layers comprising alginate having a negative charge,
      wherein an initial layer of the plurality of interfacing, individual polymer layers deposited on the charged substrate and the charged substrate have opposite charges, and
      wherein the plurality of interfacing, individual polymer layers has alternating layers of the one or more synthetic polymer layers and the one or more natural polymer layers; and
      an outer polymer layer comprising one of the one or more natural polymer layers comprising alginate;
   a chemical cross-linking agent comprising a solution of 1-ethyl-3-(3-dimethylaminopropyl)carbodiimide hydrochloride with N-hydroxysulfosuccinimide sodium salt, deposited on the outer polymer layer to immobilize fibronectin and form a modified outer surface;
   fibronectin immobilized on the modified outer surface; and
   an active substance, in addition to the fibronectin, deposited on the modified outer surface.

2. The device of claim 1, wherein the alkali metal hydroxide comprises sodium hydroxide.

3. The device of claim 1, wherein the poly-L-lysine and the alginate are each in the form of a solution and the one or more synthetic and natural polymer layers are formed by dipping the charged substrate into the solutions.

4. The device of claim 1, wherein the active substance is selected from the group consisting of drugs, biologic materials, growth factors, DNA, transfecting agents, living molecules and combinations thereof.

5. The device of claim 1, wherein the active substance is deposited on one or more of the plurality of interfacing, individual polymer layers in addition to being deposited on the modified outer surface.

* * * * *